United States Patent
Okada et al.

(10) Patent No.: US 9,708,244 B2
(45) Date of Patent: *Jul. 18, 2017

(54) COLORING MATERIAL AND METHOD FOR PRODUCING THE SAME

(71) Applicants: DAI NIPPON PRINTING CO., LTD., Tokyo-to (JP); YAMAMOTO CHEMICALS, INC., Osaka (JP)

(72) Inventors: Masato Okada, Tokyo-to (JP); Satoshi Kinoshita, Osaka (JP)

(73) Assignees: DAI NIPPON PRINTING CO., LTD., Tokyo-to (JP); YAMAMOTO CHEMICALS, INC., Yao-shi, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/436,308

(22) PCT Filed: Oct. 18, 2012

(86) PCT No.: PCT/JP2012/077003
§ 371 (c)(1),
(2) Date: Aug. 3, 2015

(87) PCT Pub. No.: WO2014/061143
PCT Pub. Date: Apr. 24, 2014

(65) Prior Publication Data
US 2015/0353472 A1    Dec. 10, 2015

(51) Int. Cl.
*C07C 211/58*    (2006.01)
*C09B 11/28*    (2006.01)
*D06P 1/42*    (2006.01)

(52) U.S. Cl.
CPC ............ *C07C 211/58* (2013.01); *C09B 11/28* (2013.01); *D06P 1/42* (2013.01)

(58) Field of Classification Search
None
See application file for complete search history.

(56) References Cited

U.S. PATENT DOCUMENTS

| | | | | |
|---|---|---|---|---|
| 4,223,144 A | * | 9/1980 | Kast | D21H 1/28 544/108 |
| 5,051,504 A | * | 9/1991 | Hahn | C07D 295/185 544/121 |
| 9,005,722 B2 | * | 4/2015 | Okada | G02B 5/223 252/586 |
| 9,266,905 B2 | * | 2/2016 | Okada | C09B 11/12 |
| 9,354,367 B2 | * | 5/2016 | Okada | C09D 11/322 |
| 2010/0192312 A1 | | 8/2010 | Cremer et al. | |
| 2011/0049444 A1 | | 3/2011 | Sako et al. | |
| 2014/0037866 A1 | | 2/2014 | Okada | |
| 2014/0039201 A1 | | 2/2014 | Okada et al. | |
| 2014/0141178 A1 | | 5/2014 | Okada | |
| 2015/0077685 A1 | | 3/2015 | Okada et al. | |

FOREIGN PATENT DOCUMENTS

| | | |
|---|---|---|
| JP | 54-50030 A | 4/1979 |
| JP | 1-269585 A | 10/1989 |
| JP | 3-24166 A | 2/1991 |
| JP | 2008-304766 A | 12/2008 |
| JP | 2010-526897 A | 8/2010 |
| JP | 2011-007847 A | 1/2011 |
| JP | 2011-213925 A | 10/2011 |
| JP | 2012-007121 A | 1/2012 |
| JP | 2012-032754 A | 2/2012 |
| JP | 2013-057052 A | 3/2013 |
| WO | 2009/107734 A1 | 9/2009 |
| WO | 2011/122707 A1 | 10/2011 |
| WO | 2011/162217 A1 | 12/2011 |
| WO | 2012/144520 A1 | 10/2012 |
| WO | 2012/144521 A1 | 10/2012 |

OTHER PUBLICATIONS

USPTO NFOA dated May 4, 2015 in connection with U.S. Appl. No. 14/112,283.
International Search Report dated Nov. 20, 2012; PCT/JP2012/077003.

* cited by examiner

*Primary Examiner* — Clinton Brooks
(74) *Attorney, Agent, or Firm* — Ladas & Parry LLP

(57) ABSTRACT

The present invention is to provide a color material with excellent dyeing property and excellent heat resistance, and a method for producing the color material, which is able to obtain the color material with high purity and at high yield. Disclosed is a color material represented by the following general formula (I):

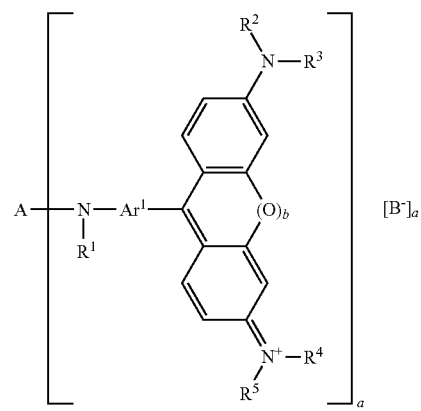

General Formula (I)

(symbols in the general formula (I) are as described in the Description.)

3 Claims, 1 Drawing Sheet

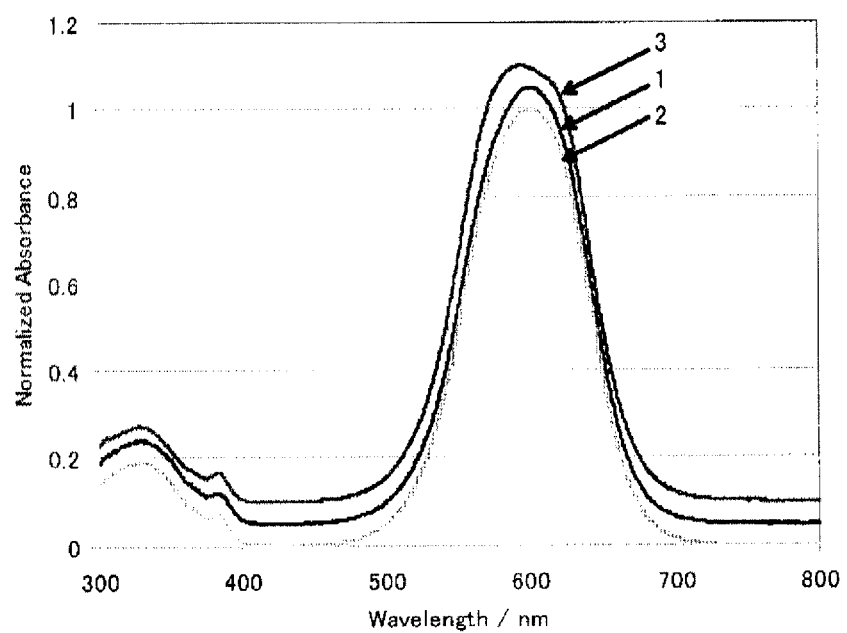

COLORING MATERIAL AND METHOD FOR PRODUCING THE SAME

TECHNICAL FIELD

The present invention relates to a novel color material with excellent heat resistance and dyeing property, and a method for producing the same.

BACKGROUND ART

Today, many dyes are known and they are broadly classified into natural dyes and synthetic dyes. Examples of the synthetic dyes include aniline blue, fuchsine and methyl orange. Most of the synthetic dyes have an aromatic or heterocyclic ring, and they are each classified as either an ionic compound (e.g., all water-soluble dye) or a nonionic compound (e.g., disperse dye). In addition, in the case of ionic dyes, they are classified into anionic dyes and cationic dyes.

The cationic dyes are made of an organic cation, which has a positive charge delocalized over a covalent bond, and an anion, which is generally inorganic. Also, they are generally dyes in which an amino group, which can have a substituent group, is involved in resonance. Therefore, the selection of cationic dyes depends on the number and type of anions, which are counter ions. Examples of counter anions include chloride ion, bromide ion, iodide ion, perchlorate ion, tetrafluoroborate ion, hexafluorophosphate ion, alkyl or aryl sulfate ion, tosylate ion, acetate or oxalate ion, etc.

In general, rhodamine, safranine and victoria blue, which are cationic dyes, have a chloride ion or tosic acid as a counter ion. However, these compounds have insufficient heat resistance.

An example in which a chloride ion or an aryl sulfate ion is used as a counter anion of a triarylmethane dye to improve heat durability of the triarylmethane dye, is known (for example, see Patent Literature 1).

In Patent Literature 2, as a method of obtaining a color composition for color filters with excellent color characteristics, heat resistance, light resistance and solvent resistance, a salt-forming compound comprising a triarylmethane basic dye and a sulfonated organic compound having at least two sulfonic groups, is disclosed.

In Patent Literature 3, as a method of obtaining a coloring resin composition which has not only excellent light resistance but also excellent light resistance, a salt forming method has been reported, in which a salt is formed by using a sulfonated compound of a dye skeleton such as phthalocyanine or anthraquinone, which is the counter anion, in combination with a triarylmethane skeleton, which is the cation.

However, the salt-forming compounds of dyes and counter anions disclosed in Patent Literatures 1 to 3 have insufficient heat resistance and insufficient fiber dyeing property, so that they have a problem of loss of color.

A polysiloxane dye is disclosed in Patent Literature 4, which is highly cross-linked by polysiloxane containing at least ten Si atoms. However, due to its synthesis method, the polysiloxane dye disclosed in Patent Literature 4 is a mixture in which an unreacted compound having only one dye skeleton or dyes with different polymerization degrees are present. Therefore, the physical properties of the dye are not stable, such as the case where, like the below-described Comparative Examples, while part of the polysiloxane dye is not dissolved in solvent, fibers dyed with the dye causes partial loss of color by washing. Also, it is difficult to separate only a dye with a specific polymerization degree from the polysiloxane dye, so that there is a problem with the productivity of the polysiloxane dye.

CITATION LIST

Patent Literature 1: Japanese Patent Application Laid-Open (JP-A) No. 2008-304766
Patent Literature 2: JP-A No. 2011-7847
Patent Literature 3: International Publication No. WO 2009/107734
Patent Literature 4: Japanese Patent Application National Publication (Laid-Open) No. 2010-526897

SUMMARY OF INVENTION

Technical Problem

The present invention was achieved in light of the above circumstances. An object of the present invention is to provide a color material with excellent dyeing property and excellent heat resistance, and a method for producing the color material, which is able to obtain the color material with high purity and at high yield.

Solution to Problem

The color material of the present invention is a compound represented by the following general formula (I):

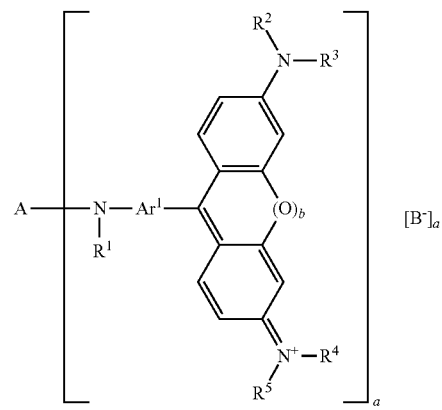

General Formula (I)

wherein A is an "a"-valent organic group in which a carbon atom directly bound to N has no n bond, and the organic group is a cyclic aliphatic hydrocarbon group having a saturated aliphatic hydrocarbon group at least at a terminal position directly bound to N, or an aromatic group having a saturated aliphatic hydrocarbon group at least at a terminal position directly bound to N, and O, S, N can be contained in a carbon chain of the organic group; $B^-$ is a monovalent anion and a plurality of $B^-$s can be the same or different; each of $R^1$ to $R^5$ is independently a hydrogen atom, an alkyl group which can have a substituent group, or an aryl group which can have a substituent group; $R^2$ and $R^3$ can be bound to form a ring structure, and/or $R^4$ and $R^5$ can be bound to form a ring structure; $Ar^1$ is a divalent polycyclic aromatic group which can have a substituent group; a plurality of $R^1$s can be the same or different; a plurality of $R^2$s can be the same or different; a plurality of $R^3$s can be the same or different; a plurality of $R^4$s can be the same or different; a plurality of $R^5$s can be the same or different; and a plurality of $Ar^1$s can be the same or different; and wherein "a" is an integer of 2 or more; "b" is 0 or 1 and there is no bond when "b" is 0; and a plurality of "b"s can be the same or different.

In the color material of the present invention, from the viewpoint of dyeing property and heat resistance, the anion ($B^-$) in the general formula (I) is preferably an organic anion having a sulfonato group ($-SO_3^-$ group).

In the color material of the present invention, from the viewpoint of dyeing property and heat resistance, the organic anion is preferably an anion represented by the following general formula (II):

General Formula (II)

wherein $Ar^2$ is a monovalent aromatic group which can have a substituent group.

The method for producing a color material represented by the following general formula (I) contains a step of carrying out a condensation reaction between a compound represented by the following general formula (A) and a compound represented by the following general formula (B):

General Formula (A)

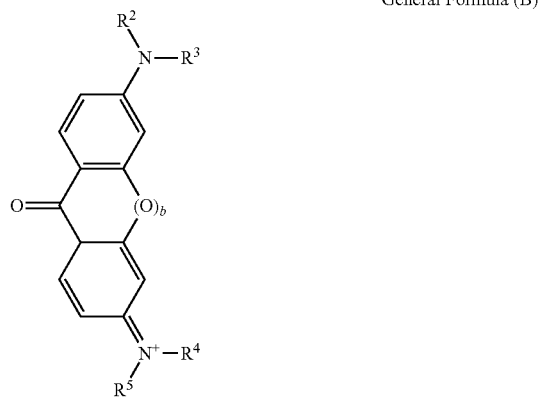

General Formula (B)

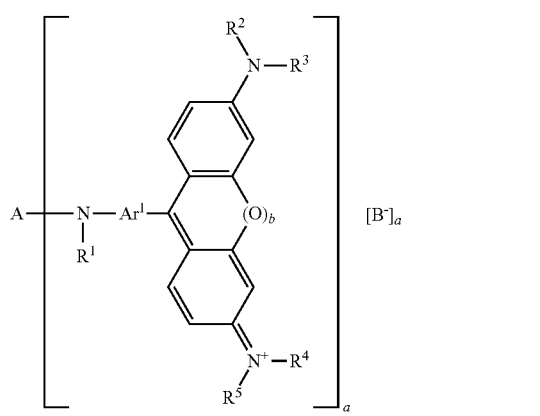

General Formula (I)

wherein A is an "a"-valent organic group in which a carbon atom directly bound to N has no π bond, and the organic group is a cyclic aliphatic hydrocarbon group having a saturated aliphatic hydrocarbon group at least at a terminal position directly bound to N, or an aromatic group having a saturated aliphatic hydrocarbon group at least at a terminal position directly bound to N, and O, S, N can be contained in a carbon chain of the organic group; $B^-$ is a monovalent anion and a plurality of $B^-$s can be the same or different; each of $R^1$ to $R^5$ is independently a hydrogen atom, an alkyl group which can have a substituent group, or an aryl group which can have a substituent group; $R^2$ and $R^3$ can be bound to form a ring structure, and/or $R^4$ and $R^5$ can be bound to form a ring structure; $Ar^1$ is a divalent polycyclic aromatic group which can have a substituent group; $Ar^{1'}$ is a monovalent polycyclic aromatic group in which a hydrogen is bound to $Ar^1$; a plurality of $R^1$s can be the same or different; a plurality of $R^2$s can be the same or different; a plurality of $R^3$s can be the same or different; a plurality of $R^4$s can be the same or different; a plurality of $R^5$s can be the same or different; a plurality of $Ar^1$s can be the same or different; and a plurality of $Ar^{1'}$s can be the same or different; and wherein "a" is an integer of 2 or more; "b" is 0 or 1 and there is no bond when "b" is 0; and a plurality of "b"s can be the same or different.

Advantageous Effects of Invention

According to the present invention, it is possible to provide a color material with excellent dyeing property and excellent heat resistance, and a method for producing the color material, which is able to obtain the color material with high purity and at high yield.

BRIEF DESCRIPTION OF DRAWING

FIG. 1 shows the absorption spectrum of color material A of Example 1, the absorption spectrum of color material C of Example 3, and the absorption spectrum of Basic Blue 7.

DESCRIPTION OF EMBODIMENTS

Hereinafter, the color material and the method for producing the same according to the present invention will be described in detail.

[Color Material]

The color material of the present invention is a compound represented by the following general formula (I):

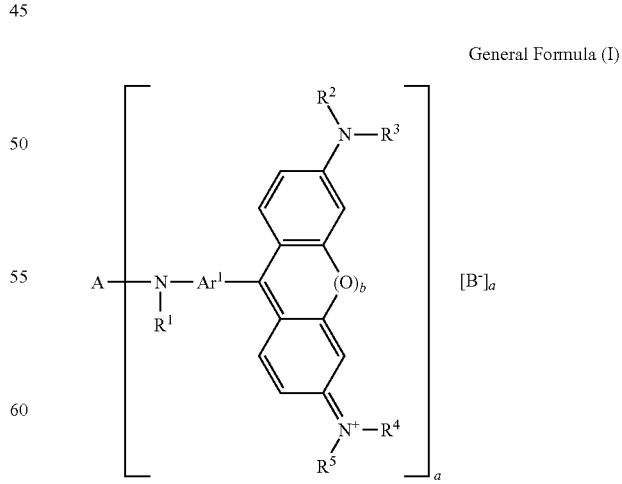

General Formula (I)

wherein A is an "a"-valent organic group in which a carbon atom directly bound to N has no π bond, and the organic group is a cyclic aliphatic hydrocarbon group having a saturated aliphatic hydrocarbon group at least at a terminal position directly bound to N, or an aromatic group having a saturated aliphatic hydrocarbon group at least at a terminal position directly bound to N, and O, S, N can be contained in a carbon chain of the organic group; $B^-$ is a monovalent anion and a plurality of $B^-$s can be the same or different; each of $R^1$ to $R^5$ is independently a hydrogen atom, an alkyl group which can have a substituent group, or an aryl group which can have a substituent group; $R^2$ and $R^3$ can be bound to form a ring structure, and/or $R^4$ and $R^5$ can be bound to form a ring structure; $Ar^1$ is a divalent polycyclic aromatic group which can have a substituent group; a plurality of $R^1$s can be the same or different; a plurality of $R^2$s can be the same or different; a plurality of $R^3$s can be the same or different; a plurality of $R^4$s can be the same or different; a plurality of $R^5$s can be the same or different; and a plurality of $Ar^1$s can be the same or different; and wherein "a" is an integer of 2 or more; "b" is 0 or 1 and there is no bond when "b" is 0; and a plurality of "b"s can be the same or different.

The color material of the present invention has excellent dyeing property and heat resistance. The reason is not clear yet; however, it is estimated as follows.

In general, dyes have a problem of low heat resistance. To overcome this problem, a method of making dyes into a salt-forming compound has been used. For example, as a method of forming a salt with a triarylmethane dye, there is a method of using a divalent anion as a counter anion (for example, Patent Literature 2). According to this method, a divalent counter anion can form ionic bonds with two dye cations, so that heat resistance is improved compared to the case of using only a dye. However, even by this method, sufficient heat resistance is not obtained. Also, since the structure of the cations is not changed, the solubility in water is not basically decreased.

In the color material of the present invention, the cationic moiety with color forming property is a divalent or higher cation having a structure represented by the following general formula (IV). Unlike the conventional triarylmethane basic dyes and xanthene basic dyes, even a chloride of the cationic moiety represented by the following general formula (IV) does not substantially dissolve in water.

If it is considered that the binding species connecting a monocation consisting of only one conventional triarylmethane skeleton and an anion is an ionic bond only, it can be considered that the binding species of the salt-forming component consisting of the divalent or higher cation of the present invention includes covalent bonds which connect monocations in addition to ionic bonds. Therefore, it is assumed that since the salt-forming component containing the divalent or higher cation having the structure represented by the following general formula (IV) contains an increased amount of stronger binding species throughout the constituent elements compared to the conventional salt-forming component containing one triarylmethane skeleton only, there is an increase in the stability of the salt-forming component and the component hardly cause hydration; moreover, there is an increase in heat resistance. Furthermore, it is assumed that since the linking group A of the structure represented by the following general formula (IV) has a structure containing a cyclic aliphatic hydrocarbon group or an aromatic group, the molecular weight and hydrophobicity of the structure represented by the following general formula (IV) are increased due to the linking group A, so that the divalent or higher cation becomes substantially insoluble in water, in cooperation with an increase in the stability of bonds. Therefore, it is assumed that even when washed with water or detergent, loss of color is not caused and excellent dyeing property is obtained.

In the color material represented by the general formula (I), the hydrocarbon of the linking group A, which is directly bound to the cationic color-forming moiety, has no π bond; therefore, the color characteristics of the cationic color-forming moiety, such as color tone and transmittance, show almost no change before and after the introduction of the linking group A.

General Formula (IV)

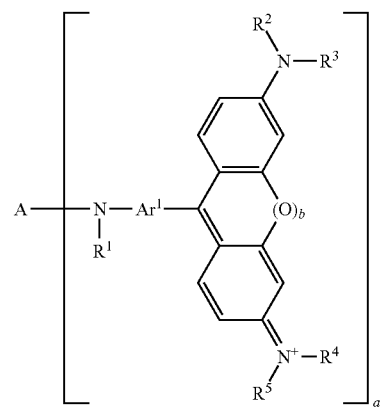

In the formula (IV), A, $R^1$ to $R^5$, $Ar^1$, "a" and "b" are the same as those in the formula (I).

In the general formula (I), "b" is an integer of 0 or 1. When "b" is 0, the present invention has a triarylmethane skeleton represented by the following formula (V). The triarylmethane skeleton shows blue color.

General Formula (V)

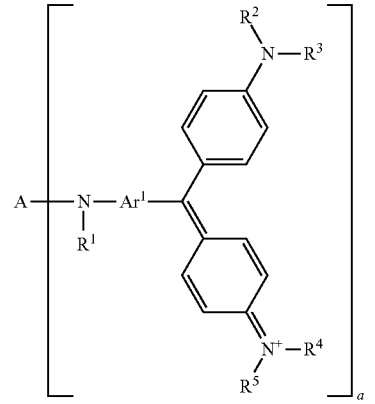

In the formula (V), A, $R^1$ to $R^5$, $Ar^1$, "a" and "b" are the same as those in the formula (I).

When "b" is 1, the present invention has a xanthene skeleton represented by the following formula (VI):

General Formula (VI)

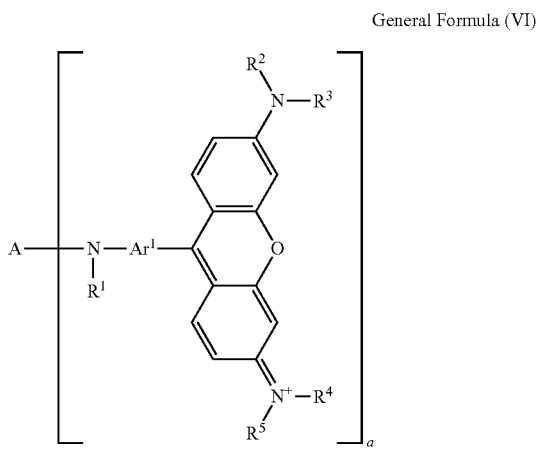

wherein A, $R^1$ to $R^5$, $Ar^1$, "a" and "b" are the same as those in the formula (I).

A plurality of "b"s can be the same or different. The examples include a cationic moiety having a plurality of triarylmethane or xanthene skeletons only, and a cationic moiety having both triarylmethane and xanthene skeletons per molecule. From the viewpoint of color purity, the cationic moiety having the same skeletons only is preferable. On the other hand, by having the cationic moiety including both triarylmethane and xanthene skeletons, or depending on the combination of substituent groups that will be described hereinafter, it is possible to adjust the color of the color material represented by the general formula (I) to a desired color.

In the general formula (I), A is an "a"-valent organic group in which a carbon atom directly bound to N (nitrogen atom) has no π bond, and the organic group is a cyclic aliphatic hydrocarbon group having a saturated aliphatic hydrocarbon group at least at a terminal position directly bound to N, or an aromatic group having a saturated aliphatic hydrocarbon group at least at a terminal position directly bound to N, and O (oxygen atom), S (sulfur atom), N (nitrogen atom) can be contained in a carbon chain of the organic group. Since the carbon atom directly bound to N has no π bond, the color characteristics of the cationic color-forming moiety, such as color tone and transmittance, are not affected by the linking group A and other color-forming moieties, thereby allowing the same color as that of a single color-forming moiety. Since A has the cyclic aliphatic hydrocarbon group or the aromatic group, the cationic skeleton has excellent toughness and excellent heat resistance.

In A, as long as the carbon atom being at the terminal position and directly bound to N has no π bond, the cyclic aliphatic hydrocarbon group having a saturated aliphatic hydrocarbon group at least at a terminal position directly bound to N, can have an unsaturated bond in carbon atoms except the one in the terminal position, have a substituent group, or contain O, S, N in the carbon chain. For example, a carbonyl group, a carboxyl group, an oxycarbonyl group and/or an amide group can be contained, and a hydrogen atom can be substituted by a halogen atom, etc.

Also in A, as the aromatic group having an aliphatic hydrocarbon group, there may be exemplified a monocyclic or polycyclic aromatic group which has a saturated aliphatic hydrocarbon group at least at the terminal position directly bound to N. The aromatic group can have a substituent group, and it can be a heterocyclic ring containing O, S, N.

As the cyclic aliphatic hydrocarbon group, a bridged alicyclic hydrocarbon group is particularly preferable from the viewpoint of skeleton toughness. The bridged alicyclic hydrocarbon group refers to a polycyclic aliphatic hydrocarbon group having a bridged structure in the aliphatic ring and having a polycyclic structure. The examples include norbornane, bicyclo[2,2,2]octane and adamantane. Of bridged alicyclic hydrocarbon groups, norbornane is preferable. Examples of the aromatic group include groups containing a benzene ring and those containing a naphthalene ring. Of them, groups containing a benzene ring are preferable.

The linking group A is preferably a cyclic aliphatic hydrocarbon group having a saturated aliphatic hydrocarbon group at a terminal position, from the point of view that the carbon atom directly bound to N is electrically stable and the stability of the cationic skeleton is increased.

From the viewpoint of availability of raw materials, A is preferably divalent. When A is a divalent organic group, examples of the divalent organic group include a straight-chain, branched-chain or cyclic alkylene group having 1 to 20 carbon atoms, and an aromatic group in which two alkylene groups each having 1 to 20 carbon atoms are bound by substitution, such as a xylylene group.

The alkyl group at each of $R^1$ to $R^5$ is not particularly limited. Examples of the alkyl group include a straight- or branched-chain alkyl group having 1 to 20 carbon atoms. Of them, preferred is a straight- or branched-chain alkyl group having 1 to 8 carbon atoms, and more preferred is a straight- or branched-chain alkyl group having 1 to 5 carbon atoms, from the viewpoint of ease of production and availability of raw materials. Of them, still more preferred is an ethyl group or a methyl group. A substituent group that the alkyl group can have is not particularly limited. The examples include an aryl group, a halogen atom and a hydroxyl group. As the substituted alkyl group, a benzyl group can be exemplified.

The aryl group at each of $R^1$ to $R^5$ is not particularly limited. The examples include a phenyl group and a naphthyl group. As a substituent group that the aryl group can have, an alkyl group and a halogen atom can be exemplified.

"$R^2$ and $R^3$ can be bound to form a ring structure, and/or $R^4$ and $R^5$ can be bound to form a ring structure" means that $R^2$ and $R^3$ form a ring structure through a nitrogen atom and/or $R^4$ and $R^5$ form a ring structure through a nitrogen atom. The ring structure is not particularly limited, and the examples include a pyrrolidine ring, a piperidine ring and a morpholine ring.

Particularly, from the viewpoint of chemical stability, it is preferable that each of $R^1$ to $R^5$ is independently a hydrogen atom, an alkyl group having 1 to 5 carbon atoms, or a phenyl group. Or, it is preferable that $R^2$ and $R^3$ are bound to form a pyrrolidine ring, a piperidine ring or a morpholine ring, and/or $R^4$ and $R^5$ are bound to form a pyrrolidine ring, a piperidine ring or a morpholine ring.

Each of $R^1$ to $R^5$ can independently have the above structure. Particularly, from the viewpoint of color purity, it is preferable that $R^1$ is a hydrogen atom. From the viewpoint of ease of production and availability of raw materials, it is more preferable that all of $R^2$ to $R^5$ are the same.

$Ar^1$ is a divalent polycyclic aromatic group. By using a polycyclic aromatic group as $Ar^1$, the cationic skeleton has excellent toughness and thus has excellent heat resistance. The polycyclic aromatic group that constitutes the polycyclic aromatic group can be a polycyclic heterocyclic group or a polycyclic aromatic hydrocarbon group composed of a carbon ring. Examples of the polycyclic aromatic hydrocarbon in the polycyclic aromatic hydrocarbon group include: condensed polycyclic aromatic hydrocarbons such as a naphthalene ring, an anthracene ring and a phenanthrene ring; and chain polycyclic aromatic hydrocarbons such as biphenyl, terphenyl, diphenylmethane, triphenylmethane and stilbene. The chain polycyclic aromatic hydrocarbon can have O, S, N in the chain skeleton, such as diphenyl ether. On the other hand, examples of the heterocyclic ring in the polycyclic heterocyclic group include: condensed polycyclic heterocyclic rings such as benzofuran, thionaphthene, indole, carbazole, coumalin, benzo-pyrone, quinoline, isoquinoline, acridine, phthalazine, quinazoline and quinoxaline. These polycyclic aromatic groups can have a substituent group.

As the substituent group that the polycyclic aromatic group can have, an alkyl group having 1 to 5 carbon atoms and a halogen atom can be exemplified.

$Ar^1$ is preferably a polycyclic aromatic group having 10 to 20 carbon atoms, more preferably a polycyclic aromatic group having a condensed polycyclic carbon ring having 10 to 14 carbon atoms. Still more preferred is a naphthylene group, from the point of view that the structure is simple and the raw materials are low-cost.

A plurality of $R^1$s per molecule can be the same or different; a plurality of $R^2$s per molecule can be the same or different; a plurality of $R^3$s per molecule can be the same or different; a plurality of $R^4$s per molecule can be the same or different; a plurality of $R^5$s per molecule can be the same or different; and a plurality of $Ar^1$s per molecule can be the same or different. The color-forming moieties can exhibit the same color when, in all of the moieties, a plurality of $R^1$s are the same; a plurality of $R^2$s are the same; a plurality of $R^3$s are the same; a plurality of $R^4$s are the same; a plurality of $R^5$s are the same; and a plurality of $Ar^1$s are the same. In this case, therefore, the color material can reproduce the same color as that of a single color-forming moiety, which is preferable from the viewpoint of color purity. On the other hand, if at least one selected from the group consisting of a plurality of $R^1$s, a plurality of $R^2$s, a plurality of $R^3$s, a plurality of $R^4$s, a plurality of $R^5$s and a plurality of $Ar^1$s is changed to a different substituent group, it is possible to reproduce a color obtained from a mixture of several kinds of color-forming moieties, so that it is possible to produce a desired color.

In the general formula (I) of the present invention, from the point of view that a blue color material with excellent dyeing property and excellent heat resistance can be obtained, the following combination is preferable: "b" is 0; $R^1$ is a hydrogen atom; each of $R^2$ to $R^5$ is an ethyl group; and $Ar^1$ is a naphthylene group.

In the color material of the present invention, the anionic moiety is a monovalent anion having a structure represented by ($B^-$). Because of having the monovalent anion, the color material of the present invention has high solubility in alcohol-based solvent and ketone-based solvent, can prepare a highly-concentrated color material solution and can be used to dye various kinds of substrates.

$B^-$ is not particularly limited, as long as it is a monovalent anion. It can be an organic or inorganic anion. "Organic anion" means an anion containing at least one carbon atom. "Inorganic anion" means an anion containing no carbon atom, and the examples include halide ions such as fluoride ion, chloride ion, bromide ion and iodide ion, and nitrate ion ($NO^-$), perchlorate ion ($ClO_4^-$), etc.

When $B^-$ is an organic anion, the structure is not particularly limited. Particularly, $B^-$ is preferably an organic group having an anionic substituent group.

Examples of the anionic substituent group include imidic acid groups such as $—SO_2N^-SO_2CH_3$, $—SO_2N^-COCH_3$, $—SO_2N^-SO_2CF_3$, $—SO_2N^-COCF_3$, $—CF_2SO_2N^-SO_2CH_3$, $—CF_2SO_2N^-COCH_3$ $—CF_2SO_2N^-SO_2CF_3$ and $—CF_2SO_2N^-COCF_3$, and substituent groups such as $—SO_3^-$, $—CF_2SO_3^-$, $—COO^-$ and $—CF_2COO^-$.

From the viewpoint of availability of raw materials, production cost, and high effect of stabilizing cations by high acidity and maintaining the state of color, imidic acid groups, $—SO_3^-$ and $—CF_2SO_3^-$ are preferable, and $SO_2^-$ (sulfonato group) is more preferable.

The organic group to which the anionic substituent group will be bound by substitution, is not particularly limited. As the organic group, there may be mentioned straight-chain, branched-chain or cyclic saturated or unsaturated hydrocarbon groups, monocyclic or polycyclic aromatic groups, and combinations thereof. In the carbon chain of these organic groups, heteroatoms such as O, S, N can be contained; a carbonyl group, a carboxy group, an oxycarbonyl group and an amide group can be contained; and a hydrogen atom can be substituted. As the substituent group that the organic group can have, there may be mentioned a halogen atom, for example.

Examples of the organic group to which the anionic substituent group will be bound by substitution, include hydrocarbons such as cyclopropane, cyclobutane, cyclopentane, cyclohexane, norbornane, bicyclo[2,2,2]hexane, bicyclo[3,2,3]octane and adamantane; and aromatic compounds such as benzene, naphthalene, anthracene, phenanthrene, pyrene, triphenylene, fluorene, furan, thiophene, pyrrole, imidazole, pyran, pyridine, pyrimidine, pyrazine, triazine, indole, purine, quinoline, isoquinoline, xanthene, carbazole, etc. In addition, the organic group can have a substituent group such as a halogen atom and an alkyl group.

As the organic group to which the anionic substituent group will be bound by substitution, monocyclic or polycyclic aromatic hydrocarbon groups and combinations thereof are particularly preferable, from the viewpoint of ease of introduction of the anionic substituent group.

In order to prevent a change in color due to the anion, it is preferable to use an organic group having an absorption maximum in a wavelength range of 400 nm or less. Examples of the organic group having an absorption maximum in a wavelength range of 400 nm or less include; organic groups composed of condensed polycyclic carbon rings such as naphthalene, tetralin, indene, fluorene, anthracene and phenanthrene; organic groups composed of chain polycyclic hydrocarbons such as biphenyl, terphenyl, diphenylmethane, triphenylmethane and stilbene; organic groups composed of five-membered heterocyclic rings such as furan, thiophene, pyrrol, oxazole, thiazole, imidazole and pyrazole; aromatic compounds composed of six-membered heterocyclic rings such as pyran, pyrone, pyridine, pyridazine, pyrimidine and pyrazine; and organic groups composed of condensed polycyclic heterocyclic rings such as benzofuran, thionaphthene, indole, carbazole, coumalin, benzo-pyrone, quinoline, isoquinoline, acridine, phthalazine, quinazoline and quinoxaline.

As the organic group to which the anionic substituent group will be bound by substitution, the following can be used: skeletons derived from azo dyes, anthraquinone dyes, triphenylmethane dyes, xanthene dyes, phthalocyanine dyes and indigo dyes, which are each an organic compound or organic metal compound. Or, there may be used conventionally-known acidic dyes, direct dyes and acidic mordant dyes.

In the case of using dye-derived skeletons, acidic dyes, direct dyes, acidic mordant dyes, etc., the color tone of the thus-obtained color material is changed, and the color tone of the color material represented by the general formula (I) can be controlled to a desired color tone.

Of anions having dye-derived skeletons, from the viewpoint of increasing heat resistance, an anion represented by the following general formula (III) is preferable.

In the case of using the anion represented by the general formula (III) as the anionic moiety of the color material of the present invention, the color material can be controlled to a desired color, depending on the cationic moiety combined therewith.

General Formula (III)

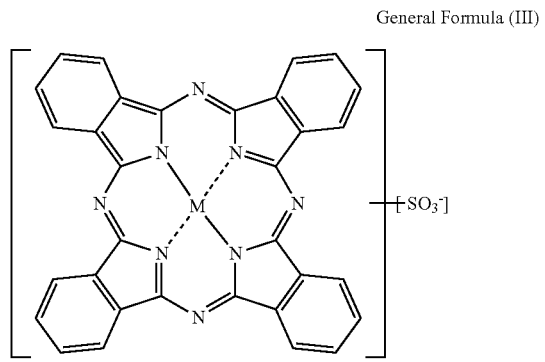

In the general formula (III), M is two hydrogen atoms or Cu, Mg, Al, Ni, Co, Fe or Zn. The sulfonato group ($-SO_3^-$ group) is bound to the aromatic ring by substitution.

Also in the color material of the present invention, from the viewpoint of increasing heat resistance, the organic anion is preferably an anion represented by the following general formula (II):

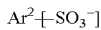 General Formula (II)

wherein $Ar^2$ is a monovalent aromatic group which can have a substituent group.

In the case of using the anion of the general formula (II) as the anionic moiety of the color material of the present invention, since the anion is colorless or light yellow, the resulting color material has such a characteristic that it is easy to maintain the color which is inherent in the cation represented by the general formula (I).

The aromatic group in $Ar^2$ is not particularly limited. The aromatic group can be a heterocyclic ring or an aromatic hydrocarbon group composed of a carbon ring. Examples of the aromatic hydrocarbon group include: a benzene ring; condensed polycyclic aromatic hydrocarbon groups such as a naphthalene ring, a tetralin ring, an indene ring, a fluorene ring, an anthracene ring and a phenanthrene ring; and chain polycyclic hydrocarbon groups such as biphenyl, terphenyl, diphenylmethane, triphenylmethane and stilbene. The chain polycyclic hydrocarbon group can have a heteroatom such as O, S in the chain skeleton, such as diphenyl ether. On the other hand, examples of the heterocyclic ring include: five-membered heterocyclic rings such as furan, thiophene, pyrrol, oxazole, thiazole, imidazole and pyrazole; six-membered heterocyclic rings such as pyran, pyrone, pyridine, pyrone, pyridazine, pyrimidine and pyrazine; and condensed polycyclic heterocyclic rings such as benzofuran, thionaphthene, indole, carbazole, coumalin, benzo-pyrone, quinoline, isoquinoline, acridine, phthalazine, quinazoline and quinoxaline. These aromatic groups can have a substituent group.

As the substituent group that the aromatic group has, an alkyl group having 1 to 5 carbon atoms and a halogen atom can be exemplified.

$Ar^2$ is preferably an aromatic group having 6 to 20 carbon atoms, more preferably an aromatic group having a condensed polycyclic carbon ring having 10 to 14 carbon atoms. Still more preferred are a phenylene group and a naphthylene group, from the point of view that the structure is simple and the raw materials are low-cost.

In the color material of the present invention, the anions (the plurality of $B^-$s) can be the same or different. Also, there may be used organic and inorganic anions in combination.

The color material of the present invention can be dissolved in a solvent and used. As the solvent to dissolve the color material of the present invention, there may be mentioned methanol, N-methylpyrrolidone (NMP), γ-butyrolactone, dimethylsulfoxide (DMSO), N,N-dimethylformamide (DMF), etc.

The color material of the present invention can be dissolved in a solvent having a solubility of the color material of 0.1 (mg/10 g solvent) or less at 23° C., that is, in a solvent in which the color material is substantially insoluble or hardly soluble. In this case, the color material is dispersed in the solvent with keeping its aggregation state, so that the heat resistance is increased higher compared to the case where the color material is dissolved in the solvent. The solvent is preferably one having a solubility of the color material of 0.01 (mg/10 g solvent) or less at 23° C., more preferably one in which the color material is substantially insoluble. Since the color material of the present invention is a normal salt, unlike the case of using an acidic salt, problems such that the dispersion of the color material does not preferably proceed or the gelation of the dispersion liquid occurs during storage, are not caused, and high dispersibility and high dispersion stability are obtained.

In the present invention, the solvent having a solubility of the color material represented by the general formula (I) of 0.1 (mg/10 g solvent) or less at 23° C., can be simply determined by the following evaluation method.

First, 10 g of a solvent to be evaluated and then 0.1 g of the color material are put in a 20 mL sample tube bottle. The tube is covered with a lid, shaken well for 20 seconds, and then left in a water bath at 23° C. for 10 minutes. Then, 5 g of the supernatant is filtered to remove insoluble substances. The thus-obtained filtrate is diluted 1,000-fold. Then, the diluted solution is measured for absorption spectrum, using a 1 cm cell in an ultraviolet and visible spectrophotometer (such as "UV-2500PC" manufactured by: Shimadzu Corporation) to calculate the absorbance at the maximum absorption wavelength. At this time, if the absorbance at the maximum absorption wavelength is less than 2, the solvent can be evaluated as a solvent having a solubility of the color material represented by the general formula (I) of 0.1 (mg/10 g solvent) or less at 23° C. (that is, a hardly-soluble solvent).

Also in the above evaluation method, the absorption spectrum is measured in the same manner as described above, without diluting the obtained filtrate, to calculate the absorbance at the maximum absorption wavelength. At this time, if the absorbance at the maximum absorption wavelength is less than 2, the solvent can be evaluated as a solvent which does not substantially dissolve the color material represented by the general formula (I).

As the solvent having a solubility of the color material of 0.1 (mg/10 g solvent) or less at 23° C., for example, there may be mentioned water and ester solvents such as ethyl acetate, butyl acetate, methyl methoxypropionate, ethyl ethoxypropionate, ethyl lactate, methoxyethyl acetate, propylene glycol monomethyl ether acetate, 3-methoxy-3-methyl-1-butyl acetate, 3-methoxybutyl acetate, methoxybutyl acetate, ethoxyethyl acetate and ethyl cellosolve acetate.

[Method for Producing the Color Material]

The method for producing the color material represented by the general formula (I) is not particularly limited. For example, the color material can be obtained by producing a cationic moiety in the following manner and then introducing a counter anion as needed.

As one method, the method for producing the color material represented by the following general formula (I) according to the present invention, contains a step of carrying out a condensation reaction between a compound represented by the following general formula (A) and a compound represented by the following general formula (B):

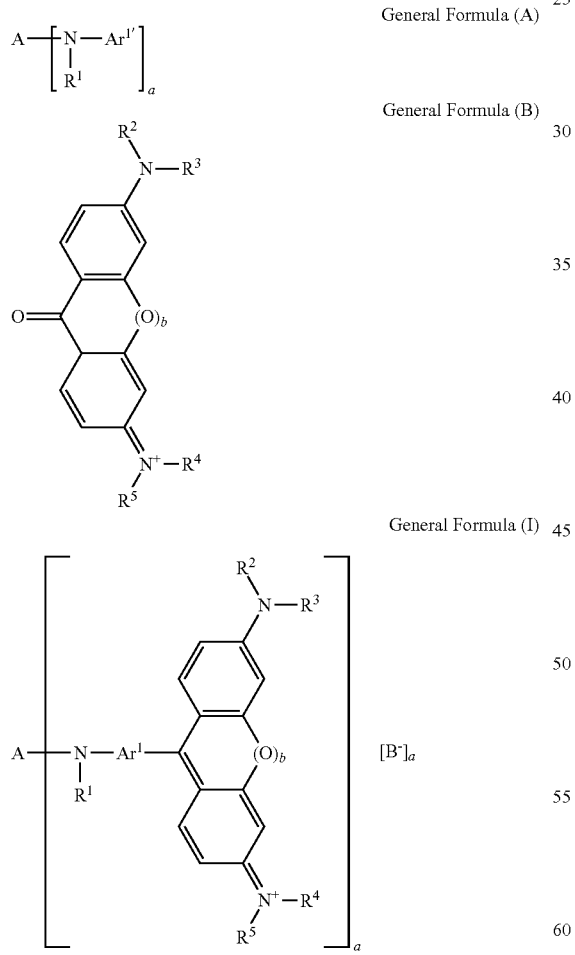

wherein A is an "a"-valent organic group in which a carbon atom directly bound to N has no n bond, and the organic group is a cyclic aliphatic hydrocarbon group having a saturated aliphatic hydrocarbon group at least at a terminal position directly bound to N, or an aromatic group having a saturated aliphatic hydrocarbon group at least at a terminal position directly bound to N, and O, S, N can be contained in a carbon chain of the organic group; $B^-$ is a monovalent anion and a plurality of $B^-$s can be the same or different; each of $R^1$ to $R^5$ is independently a hydrogen atom, an alkyl group which can have a substituent group, or an aryl group which can have a substituent group; $R^2$ and $R^3$ can be bound to form a ring structure, and/or $R^4$ and $R^5$ can be bound to form a ring structure; $Ar^1$ is a divalent polycyclic aromatic group which can have a substituent group; $Ar^{1'}$ is a monovalent polycyclic aromatic group in which a hydrogen is bound to $Ar^1$; a plurality of $R^1$s can be the same or different; a plurality of $R^2$s can be the same or different; a plurality of $R^3$s can be the same or different; a plurality of $R^4$s can be the same or different; a plurality of $R^5$s can be the same or different; a plurality of $Ar^1$s can be the same or different; and a plurality of $Ar^{1'}$s can be the same or different; and wherein "a" is an integer of 2 or more; "b" is 0 or 1 and there is no bond when "b" is 0; and a plurality of "b"s can be the same or different.

In the color material production method of the present invention, by carrying out a dehydration-condensation between $Ar^{1'}$ of the general formula (A) and the carbonyl group of the general formula (B), the linking group A is introduced at the same time as that a triarylmethane or xanthene skeleton is formed. According to this production method, color materials with different polymerization degrees are not produced, and unreacted products are largely different in skeleton and thus can be easily separated; therefore, the color material of the present invention can be obtained with high purity and at high yield.

(The compound represented by the following general formula (A))

First, the compound represented by the following general formula (A), which is a precursor compound of the cationic moiety, is synthesized. As the compound represented by the general formula (A), there may be used a commercially-available product.

General Formula (A)

In the formula (A), A, $R^1$ and "a" are the same as those in the general formula (I), and $Ar^{1'}$ is a structure in which a hydrogen is bound to $Ar^1$ of the general formula (I).

The method for synthesizing the compound represented by the general formula (A) is not particularly limited. For example, the compound can be obtained by reacting in a solvent a halogenated aromatic compound having a desired substituent group $Ar^{1'}$ introduced therein, with an "a"-valent amine compound having a desired substituent group A introduced therein, in the presence of a base and a catalyst such as palladium acetate.

The amount of the halogenated aromatic compound used in the above reaction varies depending on the desired valence (a). For example, if "a" is desired to be 2, the amount used of the halogenated aromatic compound is preferably 1.5 to 10 molar equivalent, more preferably 1.5 to 3.0 molar equivalent, still more preferably 1.8 to 2.2 molar equivalent, with respect to the amine compound, from the viewpoint of inhibiting generation of by-products and improving the reaction yield.

In the above reaction, the reaction temperature is not particularly limited and is generally around 100 to 150° C. It is preferably 130 to 145° C. from the viewpoint of inhibiting side reactions. Also in the above reaction, the reaction pressure is not particularly limited. It is preferably from an ordinary pressure to 0.1 MPa, more preferably an ordinary pressure. In the above reaction, the reaction time varies depending on the synthesis amount and the reaction temperature. It is generally set in a range of 6 to 72 hours, preferably 6 to 48 hours.

The base used in the reaction is not particularly limited. The examples include sodium hydroxide, potassium hydrate, potassium carbonate, metal alkoxides and metal amides. Particularly, it is preferable to use a strong base with low nucleophilicity, from the viewpoint of inhibiting side reactions and improving the yield of the base generator. The examples include potassium t-butoxide, sodium t-butoxide, lithium t-butoxide, lithium diisopropylamide, potassium hexamethyldisilazide and lithium tetramethylpiperidide. Of them, potassium t-butoxide is more preferable for use.

The amount of the base added is not particularly limited. With respect to the amine compound, it is generally 2.0 to 4.0 molar equivalent. From the viewpoint of improving the reaction yield, it is preferably 2.5 to 3.5 molar equivalent.

(Synthesis of the Cationic Moiety)

The cationic moiety of the color material represented by the general formula (I) is synthesized by carrying out a condensation reaction between the compound represented by the general formula (A) and the compound represented by the following general formula (B). For example, the cationic moiety of the color material represented by the general formula (I) can be obtained in the form of a chloride, by reacting the compounds in a solvent, using a chlorinating agent such as phosphorus oxychloride. As the compound represented by the following general formula (B), there may be used a commercially-available product.

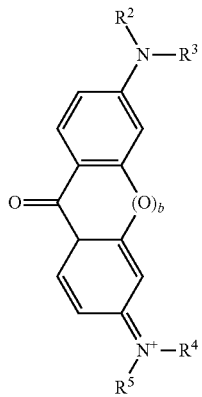

General Formula (B)

In the formula (B), $R^2$ to $R^5$ and "b" are the same as those in the general formula (I).

The amount of the compound represented by the general formula (B) and used in the above reaction varies depending on the desired valence (a). For example, if "a" is desired to be 2, the amount used of the compound represented by the general formula (B) is preferably 1.5 to 4.0 molar equivalent, more preferably 1.5 to 3.0 molar equivalent, still more preferably 1.8 to 2.2 molar equivalent, with respect to the compound represented by the general formula (A), from the viewpoint of inhibiting generation of by-products and improving the reaction yield.

The reaction temperature in the above reaction is not particularly limited and is generally around 110 to 150° C. It is preferably 110 to 120° C. from the viewpoint of inhibiting side reactions. The reaction pressure in the above reaction is not particularly limited. It is preferably from an ordinary pressure to 0.1 MPa, more preferably an ordinary pressure. The reaction time in the above reaction varies depending on the synthesis amount and the reaction temperature. It is generally set in a range of 1 to 10 hours, preferably 1 to 5 hours.

The amount of the phosphorous oxychloride added is not particularly limited. With respect to the compound represented by the general formula (A), it is generally 1.5 to 3.0 molar equivalent. From the viewpoint of improving the reaction yield, it is preferably 1.8 to 3.0 molar equivalent.

The color material represented by the general formula (I) is obtained by the above reaction, in the form of a chloride of the cationic moiety. Also, the color material which is represented by the general formula (I) and has a desired anionic moiety can be obtained by mixing, in a solvent, the chloride of the cationic moiety obtained by the reaction with a desired anionic moiety.

EXAMPLES

Hereinafter, the present invention will be described in detail, by way of examples and comparative examples. However, the scope of the present invention is not limited to these examples.

Synthesis Example 1: Synthesis of Intermediate 1

First, 18.7 g (73.4 mmol) of 1-iodonaphthalene (manufactured by Wako Pure Chemical Industries, Ltd.), 9.88 g (102.8 mmol) of sodium tert-butoxide, 5.0 g (36.7 mmol) of p-xylenediamine (manufactured by Tokyo Chemical Industry Co., Ltd.), 0.27 g (0.57 mmol) of 2-dicyclohexylphosphino-2',4',6'-triisopropylbiphenyl (manufactured by Aldrich) and 0.054 g (0.28 mmol) of palladium acetate (manufactured by Wako Pure Chemical Industries, Ltd.) were dispersed in 36 mL of xylene and reacted at 130 to 135° C. for 24 hours. After the reaction, the resultant was cooled to room temperature to precipitate crystals. The crystals were washed with methanol and then water, followed by drying, thereby obtaining 9.79 g (yield 69%) of the intermediate 1 represented by the following chemical formula (1).

From the following analysis result, the obtained compound was confirmed to be a desired compound.

MS(ESI) (m/z): 389(+)

Values of elemental analysis: CHN actual measurement values (86.72%, 6.54%, 6.97%); theoretical values (86.56%, 6.23%, 7.21%)

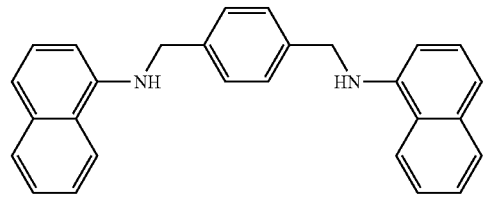

Chemical Formula (1)

Example 1: Synthesis of Color Material A

First, 10.0 g (25.7 mmol) of the intermediate 1, 100 mL of toluene, and 7.89 g (51.5 mmol) of phosphorus oxychloride (manufactured by Wako Pure Chemical Industries, Ltd.) were mixed and agitated. Next, 16.2 g (49.9 mmol) of 4,4'-bis(diethylamino)benzophenone (manufactured by Tokyo Chemical Industry Co., Ltd.) was added to the mixture, and the mixture was refluxed for 5 hours and then cooled. After the reaction, the toluene was decanted. Then, 100 mL of water was added and a resinous precipitate thus obtained was collected by filtration. The thus-obtained cake was dispersed with diluted hydrochloric acid, filtered, washed with water and then dried, thereby obtaining 18.4 g (yield 66%) of the color material A represented by the following chemical formula (2).

From the following analysis result, the obtained compound was confirmed to be a desired compound.

MS(ESI) (m/z): 501(+), divalent

Values of elemental analysis: CHN actual measurement values (78.02%, 7.13%, 7.11%); theoretical values (78.26%, 7.32%, 7.82%)

Chemical Formula (2)

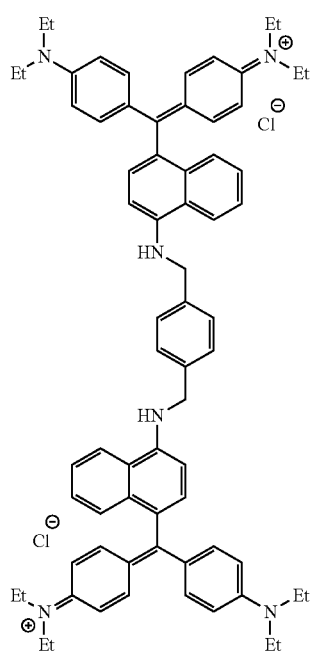

Example 2: Synthesis of Color Material B

First, 1.15 g (5.94 mmol) of sodium p-toluenesulfonate (manufactured by Tokyo Chemical Industry Co., Ltd.), 33 mL of methanol, and 33 mL of water were mixed and agitated at 50 to 55° C. Then, 3.19 g (2.97 mmol) of the color material A obtained in Example 1 was added to the mixture, and the mixture was agitated for one hour at 50 to 55° C. The methanol in the solution was evaporated with an evaporator. Then, 100 mL of water was added thereto, and a precipitate thus obtained was collected by filtration and washed with water. The thus-obtained cake was dried, thereby obtaining 3.33 g (yield 83%) of the color material B represented by the following chemical formula (3).

From the following analysis result, the obtained compound was confirmed to be a desired compound.

MS(ESI) (m/z): 502(+), divalent, 171(−) monovalent

Values of elemental analysis: CHN actual measurement values (75.18%, 7.11%, 6.15%); theoretical values (74.97%, 6.89%, 6.24%)

Chemical Formula (3)

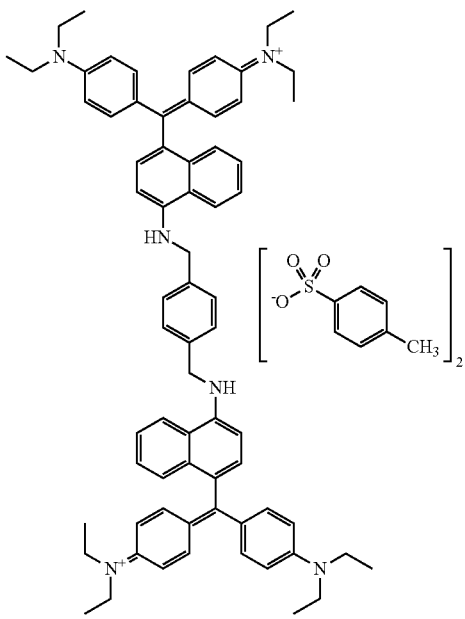

Synthesis Example 2: Synthesis of Intermediate 2

First, 15.2 g (60 mmol) of 1-iodonaphthalene (manufactured by Wako Pure Chemical Industries, Ltd.), 4.63 g (30 mmol) of norbornane diamine (NBDA) (CAS No. 56602-77-8) (manufactured by Mitsui Chemicals, Inc.), 8.07 g (84 mmol) of sodium tert-butoxide, 0.09 g (0.2 mmol) of 2-dicyclohexylphosphino-2',6',-dimethoxybiphenyl (manufactured by Aldrich) and 0.021 g (0.1 mmol) of palladium acetate (manufactured by Wako Pure Chemical Industries, Ltd.) were dispersed in 30 mL of xylene and reacted at 130 to 135° C. for 48 hours. After the reaction, the resultant was cooled to room temperature and water was added thereto. An organic phase was extracted from the resultant and dried with magnesium sulfate and then concentrated, thereby obtaining 8.5 g (yield 70%) of the intermediate 2 represented by the following chemical formula (4).

From the following analysis result, the obtained compound was confirmed to be a desired compound.

MS(ESI) (m/z): 407(M+H)

Values of elemental analysis: CHN actual measurement values (85.47%, 8.02%, 6.72%); theoretical values (85.26%, 8.11%, 6.63%)

Chemical Formula (4)

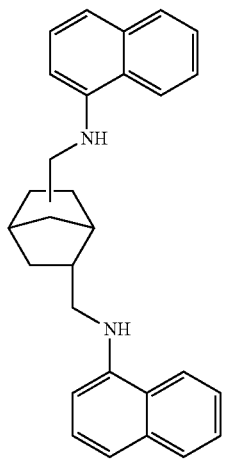

Example 3: Synthesis of Color Material C

First, 8.46 g (20.8 mmol) of the intermediate 2, 13.5 g (41.6 mmol) of 4,4'-bis(dimethylamino)benzophenone (manufactured by Tokyo Chemical Industry Co., Ltd.) and 60 mL of toluene were mixed and agitated at 45 to 50° C. Next, 6.38 g (51.5 mmol) of phosphorus oxychloride (manufactured by Wako Pure Chemical Industries, Ltd.) was added dropwise to the mixture, and the mixture was refluxed for 2 hours and then cooled. After the reaction, the toluene was decanted. A resinous precipitate thus obtained was dissolved by adding 40 mL of chloroform, 40 mL of water and concentrated hydrochloric acid to separate a chloroform phase. The chloroform phase was washed with water and dried with magnesium sulfate and then concentrated. To the thus-obtained concentrated product, 65 mL of ethyl acetate was added and refluxed. After cooling, the thus-produced precipitate was collected by filtration to obtain 15.9 g (yield 70%) of the color material C represented by the following chemical formula (5).

From the following analysis result, the obtained compound was confirmed to be a desired compound.
MS(ESI) (m/z): 511(+), divalent
Values of elemental analysis: CHN actual measurement values (78.13%, 7.48%, 7.78%); theoretical values (78.06%, 7.75%, 7.69%)

Chemical Formula (5)

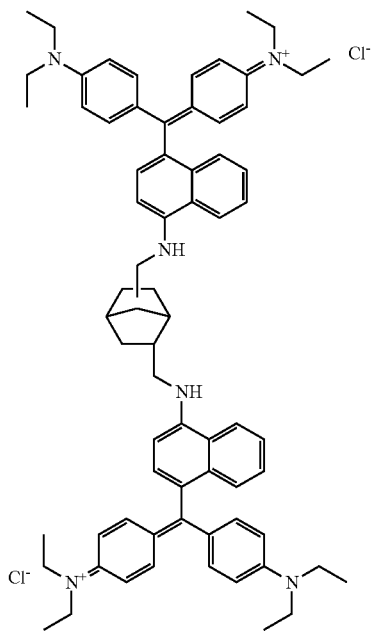

Comparative Example 1: Color Material D

Basic Blue 7 (CI-42595) (BB7) (manufactured by Tokyo Chemical Industry Co., Ltd.) represented by the following chemical formula (6) was used as the color material D of Comparative Example 1.

Chemical Formula (6)

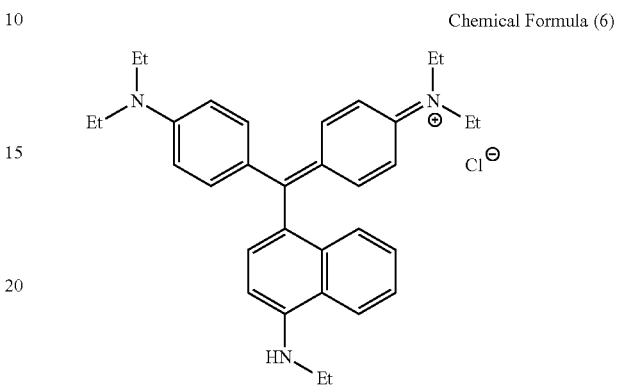

Comparative Example 2: Synthesis of Color Material E

First, 0.97 g (5.02 mmol) of sodium p-toluenesulfonate (manufactured by Tokyo Chemical Industry Co., Ltd.) was dissolved in 50 mL of water and 50 mL of methanol. Then, 5.0 g (9.73 mmol) of Basic Blue 7 (CI-42595) (manufactured by Tokyo Chemical Industry Co., Ltd.) was added thereto and agitated for one hour at ordinary temperature. The thus-obtained reaction solution was filtered at reduced pressure, thus obtaining a cake. The cake was washed with water and then dried at reduced pressure, thus obtaining 3.0 g (yield 92%) of the color material E represented by the following chemical formula (7).

Chemical Formula (7)

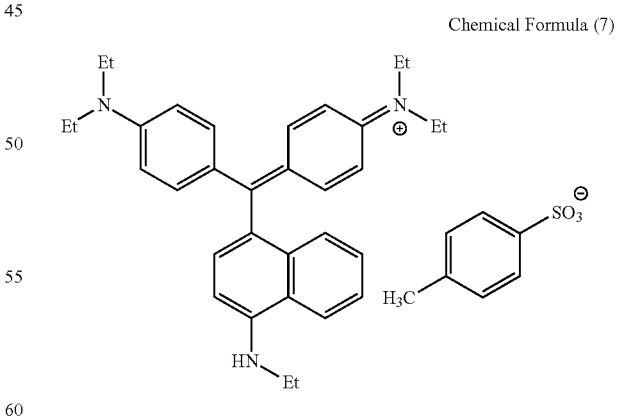

Comparative Example 3: Synthesis of Color Material F

First, 1.62 g (5.02 mmol) of disodium naphthalene 2,6-sulfonate (manufactured by Tokyo Chemical Industry Co., Ltd.) was dissolved in 50 mL of water and 50 mL of methanol. Then, 5.0 g (9.73 mmol) of Basic Blue 7 (CI-42595) (manufactured by Tokyo Chemical Industry Co., Ltd.) was added thereto and agitated for one hour at ordinary temperature. The thus-obtained reaction solution was filtered at reduced pressure, thus obtaining a cake. The cake was washed with water and then dried at reduced pressure, thus obtaining 5.2 g (yield 86%) of the color material F represented by the following chemical formula (8).

Chemical Formula (8)

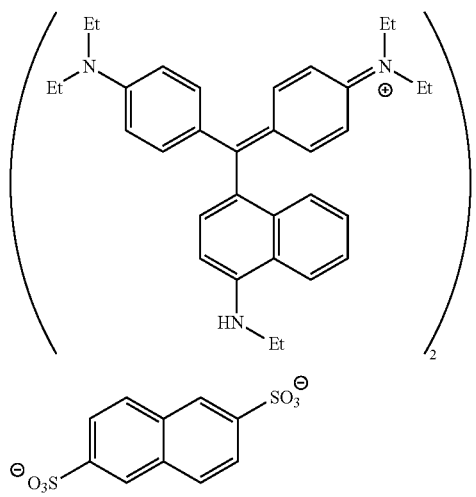

Comparative Example 4: Synthesis of Color Material G

The color material G represented by the following chemical formula (9) was obtained in the same manner as Comparative Example 3, except that 3.92 g (5.02 mmol) of Direct Blue 86 (manufactured by Tokyo Chemical Industry Co., Ltd.) was used in place of the disodium naphthalene 2,6-sulfonate.

Chemical Formula (9)

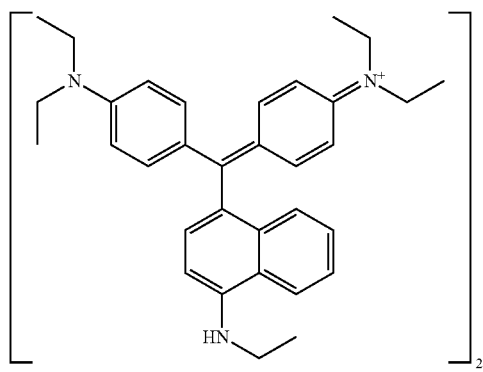

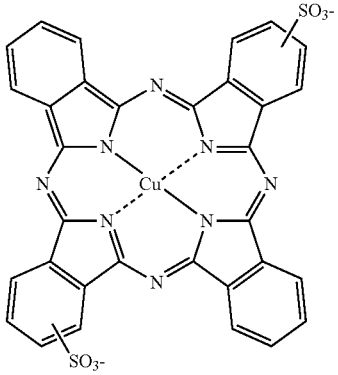

Comparative Example 5: Synthesis of Color Material H

In accordance with the method disclosed in Patent Literature 4, 12-molybdophosphate of polysiloxane dye was synthesized to obtain the color material H.

First, 51.52 g of Basic Blue 7 (BB7) (manufactured by Tokyo Chemical Industry Co., Ltd.) was dissolved in 750 ml of ion-exchanged water. Then, an aqueous solution of 2N sodium hydroxide was added thereto, with agitation, until the deprotonated form of the dye was completely precipitated and no blue color remained in the solution and did not return for several hours. The thus-produced precipitate was collected by filtration, washed three times with ion-exchanged water, and then dried at 60° C. under reduced pressure (0.1 kPa). Therefore, 45.23 g (94.7%) of deprotonated BB7 was separated in the form of nearly black powder.

Separately, 50 ml of 3-iodopropyl-trimethoxysilane (manufactured by Sigma-Aldrich) and 2.0 ml (2.95 g; 10.2 mmol) of an anhydrous ethanol solution were mixed and then agitated at room temperature for 60 hours under an argon flow. Then, the solvent was distilled away under reduced pressure to obtain 3-iodopropyl-triethoxysilane. The thus-obtained 3-iodopropyl-triethoxysilane was dissolved in 50 ml of anhydrous acetonitrile, and 2.389 g (5 mmol) of the above-mentioned deprotonated BB7 was added thereto. Then, under an argon flow, the thus-obtained solution was refluxed under heating for 24 hours. After the solvent was distilled away from the solution, a semisolid residue thus obtained was washed several times with methyl-t-butyl ether, under an argon flow, to remove the excess of alkylating agent and the unreacted deprotonated dye, until the filtrate was nearly colorless. A solid residue was separated therefrom, which is silanized BB7. Then, 1 g of the silanized BB7 was dissolved in 25 ml of anhydrous ethanol to obtain a silanized BB7 solution.

Then, 25 ml of the silanized BB7 solution was added to a mixed solvent of 150 ml of ethanol (96%), 50 ml of water and 30 g of a 25% ammonia aqueous solution and agitated vigorously at room temperature for 24 hours to form seed particles. Then, the mixture was subjected to centrifugation. A residue thus obtained was dispersed in ethanol (80%) and subjected to three cycles of washing and centrifugation. Thereafter, the solvent was removed therefrom to obtain a residue. The thus-obtained residue was dispersed in dimethyl sulfoxide (DMSO), added in 400 ml of deionized water and agitated. Furthermore, 12-molybdophosphoric acid n-hydrate was added thereto, thereby obtaining the color material H of Comparative Example 5.

<Evaluation of Color Change in Color Materials>

First, 10 mg of each of the color materials A and C obtained in Examples 1 and 3 was dissolved in 100 mL of methanol and diluted 20-fold, thereby obtaining a measurement solution. The absorption spectrum of the solution was measured by using a 1 cm quarts cell in spectrophotometer U-3500 manufactured by Hitachi, Ltd.

Next, 10 mg of BB7 (monomer) was dissolved in 100 mL of methanol and diluted 20-fold, thereby obtaining a measurement solution as a control product. The absorption spectrum of the solution was measured by the same method as above. The results are shown in FIG. 1.

From the results shown in FIG. 1, it is clear that the color materials A and C have almost the same peak forms as the BB7 having no linking group, and there is almost no change in color.

As just described, it is clear that the color material which is represented by the general formula (I) and has the linking group in which the carbon atom directly bound to N has no π bond, has the same color as the color material of the monomer having no linking group.

<Evaluation of Solubility in Methanol>

First, 0.05 g of each of the color materials A to H of Examples 1 to 3 and Comparative Examples 1 to 5 was put in a sample tube bottle. Methanol (manufactured by Kanto Chemical Co., Inc.) was added thereto so that the total weight (excluding the sample tube bottle) was 1.0 g. Magnetic stirrers were put in the bottle and the mixture was agitated at room temperature for one hour. Then, the mixture was visually observed whether the color material was dissolved or not. When the color material was dissolved, the color material was regarded as ○. When insoluble substances were found, the color material was regarded as x.

<Evaluation of Heat Resistance>

(1) Evaluation of Thermal Decomposition Temperature

First, about 5 mg of each of the color materials A to H of Examples 1 to 3 and Comparative Examples 1 to 5 was put in a quarts pan. As a reference, alumina was put in a quarts pan. Using horizontal differential thermogravimetric-differential thermal analyzer (TG-DTA) TG8120 (manufactured by Rigaku Corporation), they were measured at a heating rate of 5° C./min to 800° C. The extrapolated temperature of the peak of the thus-obtained TG curve was used as a decomposition point, and the temperature at the decomposition point was used as a thermal decomposition temperature. The thermal decomposition temperature can be used as an indicator of heat resistance.

(2) Evaluation of Weight Reduction Rate

First, about 5 mg of each of the color materials A to H of Examples 1 to 3 and Comparative Examples 1 to 5 was put in a quarts pan. As a reference, alumina was put in a quarts pan. Using differential thermogravimetric analyzer (TG-DTA) TG8120 (manufactured by Rigaku Corporation), they were heated to 230° C. at a heating rate of 20° C./min. From the time when they reached 230° C., they were kept at the same temperature for 60 minutes and then measured for the weight reduction rate. The weight reduction rate is calculated by the following formula and can be used as an indicator of heat resistance.

Weight reduction rate=("weight before heating"−"weight after heating")/"weight before heating"×100(%)

<Evaluation of Dyeing Property>

(1) Fabric Dyeing

First, 0.5 g of the color material A of Example 1 was mixed with 10 ml of methanol to obtain a methanol solution of the color material A. Next, 0.1 ml of the methanol solution was placed dropwise on a fabric, and the methanol was removed by a drier, thereby dyeing the fabric with the color material A.

Also, fabrics were dyed with the color materials B to H in the same manner as above, except that the color materials B to H were each used in place of the color material A.

(2) Evaluation by Using Water

The fabrics dyed with the color materials A to H were washed with running water at 20° C. for 10 minutes. They were visually observed whether there was a loss of color and evaluated according to the following evaluation criterion:

[Evaluation Criterion]

○: There was no loss of color from the fabric

Δ: There was a loss of color from the fabric x: No color remained on the fabric (3) Evaluation by Using Detergent The fabrics dyed with the color material A to H were immersed in a surfactant-containing detergent for 5 minutes and then washed with running water at 20° C. for 5 minutes. They were visually observed whether there was a loss of color and evaluated according to the same valuation criteria as above.

The evaluation results are shown in Table 1.

TABLE 1

| | Color material | a | Structure of color material | | Solubility (Methanol) | Evaluation of heat resistance | | Evaluation of dyeing property | |
|---|---|---|---|---|---|---|---|---|---|
| | | | Cation | Anion | | Thermal decomposition temperature (° C.) | Weight reduction rate (%) (230° C. for 1 hr) | Washed with running water | Immersed in detergent and then washed with running water |
| Example 1 | A | 2 | BB7-Xy-dimer | Cl⁻ | ○ | 247 | −28.9 | ○ | ○ |
| Example 2 | B | 2 | ↑ | CH₃—C₆H₅—SO₃⁻ | ○ | 255 | −29.1 | ○ | ○ |
| Example 3 | C | 2 | BB7-Nb-dimer | Cl⁻ | ○ | 244 | −28.2 | ○ | ○ |
| Comparative Example 1 | D | 1 | BB7 | ↑ | ○ | 218 | −40.2 | x | x |
| Comparative Example 2 | E | 1 | ↑ | CH₃—C₆H₅—SO₃⁻ | ○ | 245 | −38.3 | Δ | x |
| Comparative Example 3 | F | 1 | ↑ | 2,6-Naph-(SO₃⁻)₂ | ○ | 236 | −33.8 | Δ | x |

TABLE 1-continued

| | Color material | a | Structure of color material Cation | Anion | Solubility (Methanol) | Evaluation of heat resistance Thermal decomposition temperature (° C.) | Evaluation of heat resistance Weight reduction rate (%) (230° C. for 1 hr) | Evaluation of dyeing property Washed with running water | Evaluation of dyeing property Immersed in detergent and then washed with running water |
|---|---|---|---|---|---|---|---|---|---|
| Comparative Example 4 | G | 1 | ↑ | CuPc—(SO$_3^-$)$_2$ | ○ | 250 | −33.2 | ○ | x |
| Comparative Example 5 | H | ≥1 | —((BB7-Pr)—Si(OMe)$_2$O)— | Cl$^-$ | x (Insoluble substances were found) | 232 | −42.3 | ○ | Δ |

CONCLUSION

It is clear that the color materials A to C of Examples 1 to 3, represented by the general formula (I), have excellent dyeing property and heat resistance.

The color material of Comparative Example 1, which is a conventional triarylmethane-based dye, has insufficient heat resistance and dyeing property. Comparative Examples 2 to 4 shows that the heat resistance and dyeing property of the color materials were improved by changing the anion; however, they are still insufficient, and a loss of color was easily caused by household detergent.

The color material of Comparative Example 5 contains the cation which has such a structure that the triarylmethane-based dye was polymerized by siloxane. However, the color material is a mixture of dyes with different polymerization degrees, so that the heat resistance and dyeing property are insufficient, and insoluble substances were found in methanol.

REFERENCE SIGNS LIST

1. The absorption spectrum of the color material A obtained in Example 1
2. The absorption spectrum of the color material C obtained in Example 3
3. The absorption spectrum of Basic Blue 7

The invention claimed is:

1. A color material represented by the following general formula (I):

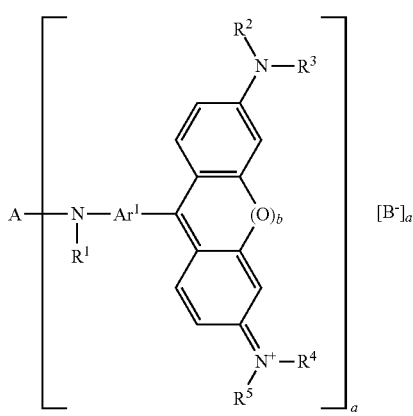

General Formula (I)

wherein A is an "a"-valent organic group in which a carbon atom directly bound to N has no π bond, and the organic group is a cyclic aliphatic hydrocarbon group having a saturated aliphatic hydrocarbon group at least at a terminal position directly bound to N, and O, S, N can be contained in a carbon chain of the organic group; $B^-$ is a monovalent organic anion having a sulfonate group (—SO$_3^-$ group) and a plurality of $B^-$s can be the same or different; each of $R^1$ to $R^5$ is independently a hydrogen atom, an alkyl group which can have a substituent group, or an aryl group which can have a substituent group; $R^2$ and $R^3$ can be bound to form a ring structure, and/or $R^4$ and $R^5$ can be bound to form a ring structure; $Ar^1$ is a divalent polycyclic aromatic group which can have a substituent group; a plurality of $R^1$s can be the same or different; a plurality of $R^2$s can be the same or different; a plurality of $R^3$s can be the same or different; a plurality of $R^4$s can be the same or different; a plurality of $R^5$s can be the same or different; and a plurality of $Ar^1$s can be the same or different; and wherein "a" is an integer of 2 or more; "b" is 0 or 1 and there is no bond when "b" is 0; and a plurality of "b"s can be the same or different.

2. The color material according to claim 1, wherein the organic anion is an anion represented by the following general formula (II):

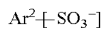

General Formula (II)

wherein $Ar^2$ is a monovalent aromatic group which can have a substituent group.

3. A method for producing the color material represented by general formula (I) of claim 1, the method comprising:
a step of carrying out a condensation reaction between a compound represented by the following general formula (A) and a compound represented by the following general formula (B) to produce the general formula (I),

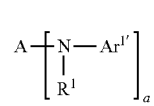

General Formula (A)

-continued

General Formula (B)

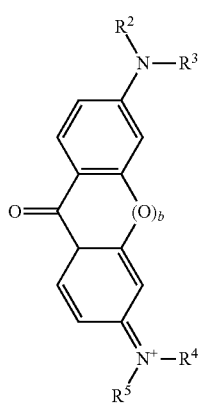

General Formula (I)

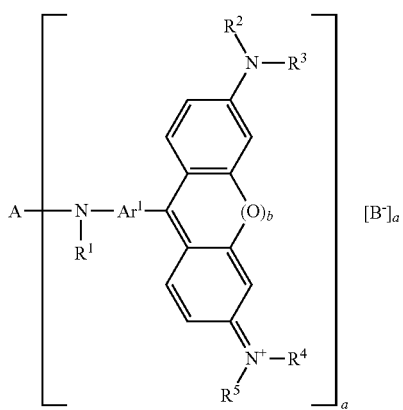

wherein A is an "a"-valent organic group in which a carbon atom directly bound to N has no πbond, and the organic group is a cyclic aliphatic hydrocarbon group having a saturated aliphatic hydrocarbon group at least at a terminal position directly bound to N, and O, S, N can be contained in a carbon chain of the organic group; $B^-$ is a monovalent organic anion having a sulfonate group ($—SO_3^-$ group) and a plurality of $B^-$s can be the same or different; each of $R^1$ to $R^5$ is independently a hydrogen atom, an alkyl group which can have a substituent group, or an aryl group which can have a substituent group; $R^2$ and $R^3$ can be bound to form a ring structure, and/or $R^4$ and $R^5$ can be bound to form a ring structure; $Ar^1$ is a divalent polycyclic aromatic group which can have a substituent group; $Ar^{1'}$ is a monovalent polycyclic aromatic group in which a hydrogen is a bound to $Ar^1$; a plurality of $R^1$s can be the same or different; a plurality of $R^2$s can be the same or different; a plurality of $R^3$s can be the same or different; a plurality of $R^4$s can be the same or different; a plurality of $R^5$s can be the same or different; a plurality of $Ar^1$s can be the same or different; a plurality of $Ar^{1'}$s can be the same or different; and wherein "a" is an integer of 2 or more; "b" is 0 or 1 and there is no bond when "b" is 0; and a plurality of "b"s can be the same or different.

* * * * *